(12) United States Patent
Gawande et al.

(10) Patent No.: US 11,103,433 B2
(45) Date of Patent: *Aug. 31, 2021

(54) ANTIMICROBIAL-ANTIBIOFILM COMPOSITIONS AND METHODS OF USE THEREOF FOR PERSONAL CARE PRODUCTS

(71) Applicant: KANE BIOTECH INC., Winnipeg (CA)

(72) Inventors: Purushottam V. Gawande, Winnipeg (CA); Karen Lovetri, Winnipeg (CA); Nandadeva Yakandawala, Winnipeg (CA); Gord Froehlich, Selkirk (CA); Srinivasa Madhyastha, Winnipeg (CA)

(73) Assignee: KANE BIOTECH INC., Winnipeg (CA)

(*) Notice: Subject to any disclaimer, the term of this patent is extended or adjusted under 35 U.S.C. 154(b) by 0 days.

This patent is subject to a terminal disclaimer.

(21) Appl. No.: 15/322,385

(22) PCT Filed: Jun. 26, 2015

(86) PCT No.: PCT/CA2015/050599
§ 371 (c)(1),
(2) Date: Dec. 27, 2016

(87) PCT Pub. No.: WO2015/196299
PCT Pub. Date: Dec. 30, 2015

(65) Prior Publication Data
US 2017/0128338 A1    May 11, 2017
US 2019/0076345 A9    Mar. 14, 2019

Related U.S. Application Data

(63) Continuation-in-part of application No. 14/355,308, filed as application No. PCT/CA2012/050432 on Jun. 27, 2012.

(Continued)

(51) Int. Cl.
*A61K 8/44* (2006.01)
*A01N 37/44* (2006.01)
(Continued)

(52) U.S. Cl.
CPC ............... *A61K 8/44* (2013.01); *A01N 37/04* (2013.01); *A01N 37/44* (2013.01); *A01N 59/16* (2013.01);
(Continued)

(58) Field of Classification Search
CPC .......... A61K 8/44; A61K 8/365; A61K 3/125; A61K 8/362; A61K 9/0048; A61K 45/06;
(Continued)

(56) References Cited

U.S. PATENT DOCUMENTS 3,887,712 A    6/1975   Lover et al.
4,060,600 A    11/1977  Vit
(Continued)

FOREIGN PATENT DOCUMENTS

CN    101756794 A    6/2010
WO    9418939 A1    9/1994
(Continued)

OTHER PUBLICATIONS

Shanks, Robert M.Q. et al. "Catheter Lock Solutions Influence Staphylococcal Biofilm Formation on Abiotic Surfaces", Nephrol. Dial Transplant, 21, pp. 2247-2255.

(Continued)

*Primary Examiner* — Robert A Wax
*Assistant Examiner* — Quanglong N Truong
(74) *Attorney, Agent, or Firm* — Nelson Mullins Riley & Scarborough LLP; Thomas J. Engellenner; Reza Mollaaghababa

(57) ABSTRACT

Compositions comprising one or more chelating agents and optionally zinc ion salts are used to inhibit the growth or (Continued)

biofilm formation in bacteria associated with personal care products such as ophthalmic, pedicure, manicure or podiatric solutions. The compositions of the present application can also comprise gelling agents, antimicrobials, antibiotic or a pH adjuster. The compositions may be in the form of a solution, a gel, a cream, a jelly, a powder, a paste, a lotion, soap and a cleaner.

15 Claims, 11 Drawing Sheets

Related U.S. Application Data

(60) Provisional application No. 62/018,114, filed on Jun. 27, 2014.

(51) Int. Cl.

| | | |
|---|---|---|
| A01N 59/16 | (2006.01) | |
| A61K 8/27 | (2006.01) | |
| A61Q 3/00 | (2006.01) | |
| A61K 31/194 | (2006.01) | |
| A61K 31/198 | (2006.01) | |
| A61K 33/30 | (2006.01) | |
| A61Q 17/00 | (2006.01) | |
| A61K 8/365 | (2006.01) | |
| A61B 3/125 | (2006.01) | |
| A61C 11/00 | (2006.01) | |
| A01N 37/04 | (2006.01) | |
| A61K 8/362 | (2006.01) | |
| A61K 9/00 | (2006.01) | |
| A61K 45/06 | (2006.01) | |

(52) U.S. Cl.
CPC .......... *A61B 3/125* (2013.01); *A61C 11/005* (2013.01); *A61K 8/27* (2013.01); *A61K 8/362* (2013.01); *A61K 8/365* (2013.01); *A61K 9/0048* (2013.01); *A61K 31/194* (2013.01); *A61K 31/198* (2013.01); *A61K 33/30* (2013.01); *A61K 45/06* (2013.01); *A61Q 3/00* (2013.01); *A61Q 17/005* (2013.01); *A61K 2800/70* (2013.01); *Y02A 50/30* (2018.01)

(58) Field of Classification Search
CPC ...... A61K 8/27; A61K 31/194; A61K 31/198; A61K 33/30; A61K 2800/70; A61B 3/125; A61C 11/005; A01N 37/04; A01N 37/44; A01N 59/16; A61Q 17/005; A61Q 3/00; Y02A 50/30; Y02A 50/47; Y02A 50/481; Y02A 50/471; Y02A 50/473; A61P 31/10; A61P 31/04; A61P 31/00; A61P 27/02; A61P 17/00
See application file for complete search history.

(56) References Cited

U.S. PATENT DOCUMENTS

| | | |
|---|---|---|
| 4,119,711 A | 10/1978 | Hernestam et al. |
| 4,160,821 A | 7/1979 | Sipos |
| 4,178,363 A | 12/1979 | Miller, Jr. |
| 4,610,871 A | 9/1986 | Lynch |
| 4,999,184 A | 3/1991 | Parran, Jr. et al. |
| 5,104,644 A | 4/1992 | Douglas |
| 5,174,990 A | 12/1992 | Douglas |
| 5,310,546 A | 5/1994 | Douglas |
| 5,624,906 A * | 4/1997 | Vermeer .................. A61K 8/60 |
| | | 514/23 |
| 5,932,469 A | 8/1999 | Hillman |
| 6,218,362 B1 | 4/2001 | Lavoie et al. |
| 6,294,186 B1 * | 9/2001 | Beerse .................. A01N 43/36 |
| | | 424/401 |
| 6,342,385 B1 | 1/2002 | Qi et al. |
| 6,391,285 B1 | 5/2002 | Hillman |
| 6,475,771 B1 | 11/2002 | Hillman |
| 6,589,562 B1 | 7/2003 | Shefer et al. |
| 6,696,047 B2 | 2/2004 | Scott |
| 6,699,839 B1 | 3/2004 | Lavoie et al. |
| 6,699,970 B2 | 3/2004 | Qi et al. |
| 7,597,895 B2 | 10/2009 | Huang et al. |
| 9,980,497 B2 * | 5/2018 | Gawande ................. A23B 4/20 |
| 10,357,470 B2 * | 7/2019 | Gawande ............. A61K 31/194 |
| 2004/0127372 A1 * | 7/2004 | Ketelson .................. C11D 1/10 |
| | | 510/112 |
| 2005/0101605 A1 | 5/2005 | Ahmed et al. |
| 2005/0170013 A1 * | 8/2005 | Douglas ............... A61K 31/198 |
| | | 424/616 |
| 2006/0140876 A1 | 6/2006 | Balasch Risueno et al. |
| 2007/0190005 A1 * | 8/2007 | Rozsa ..................... A61K 8/368 |
| | | 424/70.1 |
| 2009/0221483 A1 * | 9/2009 | Melgarejo .............. C07K 14/47 |
| | | 514/1.1 |
| 2010/0106103 A1 * | 4/2010 | Ziebol ..................... A61L 2/186 |
| | | 604/265 |
| 2010/0106210 A1 | 4/2010 | Hedberg et al. |
| 2011/0008402 A1 * | 1/2011 | Madhyastha .......... A61L 15/46 |
| | | 424/405 |
| 2011/0171283 A1 * | 7/2011 | Riesinger .............. A61K 9/0014 |
| | | 424/445 |
| 2012/0107258 A1 * | 5/2012 | Kuhn ....................... A61K 8/34 |
| | | 424/65 |

FOREIGN PATENT DOCUMENTS

| | | | |
|---|---|---|---|
| WO | 2003/047341 A2 | 6/2003 | |
| WO | 2005/097067 A1 | 10/2005 | |
| WO | 2006068753 A1 | 6/2006 | |
| WO | 2006089139 A2 | 8/2006 | |
| WO | WO-2013063695 A1 * | 5/2013 | ............. A61K 38/40 |
| WO | 2014/100777 A2 | 6/2014 | |
| WO | 2014/134701 A1 | 9/2014 | |

OTHER PUBLICATIONS

International Search Report and Written Opinion for corresponding International Application PCT/CA2015/050599, dated Sep. 22, 2015.
Steven Opal, Clinical Gram-positive sepsis: Does it fundamentally differ from Gram-negative bacterial sepsis?, Critical care Medicine, Issue: vol. 27(8), 1999, pp. 1-14.
"Oral Health in America", published by the National Institute of Dental and Craniofacial Research in 2000. Chapter 3 Diseases and Disorders is on pp. 37-60.
Stedman's Medical Dictionary, Definition of Analogue, accessed on Oct. 19, 2018.
N. Yakandawala, Effect of ovotransferrin, protamine sulfate and EDTA combination on biofilm formation by catheter-associated bacteria, Journal of Applied Microbiology 102 (2007) 722-727.

* cited by examiner

ANTIMICROBIAL-ANTIBIOFILM COMPOSITIONS AND METHODS OF USE THEREOF FOR PERSONAL CARE PRODUCTS

CROSS-REFERENCE TO RELATED APPLICATIONS

This application is a National Phase Entry of International Application No. PCT/CA2015/050599, filed Jun. 26, 2015, which claims the benefit of U.S. Provisional Application No. 62/018,114, entitled "ANTIMICROBIAL-ANTIBIOFILM COMPOSITIONS AND METHODS OF USE THEREOF FOR PERSONAL CARE PRODUCTS" filed on Jun. 27, 2014. This application is also a continuation-in-part of U.S. application Ser. No. 14/355,308 filed on Oct. 7, 2014, which is the U.S. National Stage of International Application No. PCT/CA2012/050432 filed on Jun. 27, 2012.

FIELD OF THE INVENTION

This invention may relate to methods of using antimicrobial and antibiofilm compositions for personal care products. It further may relate to methods of formulating the compositions comprising chelating agents, zinc salts, antimicrobials and personal care acceptable excipients for applications in personal care products. More particularly, the invention may relate to an efficient method of delivering acceptable formulations containing two or more chelating agents and a zinc salt for personal care.

BACKGROUND OF THE INVENTION

Contact lenses are used by an increasing number of people as means of correcting vision and/or compensating for eye abnormalities. Contact lenses usually must be inserted and removed daily with cleaning and disinfection between each wearing that requires solutions and containers. During wear and normal handling of contact lenses, microorganisms can adhere to the contact lenses and contaminate the storage containers/solution. Then, microorganisms that multiplied in the storage containers/solution can transfer to the eyes via contact lenses and become a pathogen that may cause eye infection. Various solutions have been developed to clean these deposits and disinfect the containers.

Daily cleaners, comprised with various kinds of surfactants and disinfectants is recommended for daily use to remove most deposits and debris on contact lenses.

Solutions that wet the lenses before insertion in the eye are required for contact lenses. After the contact lenses are inserted in the eye, ophthalmic solutions for rewetting, lubricating, and/or enhancing the comfort of the contact lens wearer are sometimes applied to the eye by means of a drop dispenser. Solutions for improving the comfort of wearing soft contact lenses by being added directly to the contact lens in the eye typically contain viscosity enhancing agents, lubricants, surfactants, buffers, preservatives, and salts.

Multipurpose solutions are popular because of the convenience of a single solution for cleaning, disinfecting and conditioning contact lenses immediately prior to insertion of the lens in the eye. Multipurpose solutions are also designed for use as a wetting agent, without rinsing, meaning that the solution must be ophthalmically safe for eye contact. This limits, to some extent, the type and concentration of both cleaning agents, biocides, antibacterials, and antibiofilm agents that can be employed in the solution as a preservative or disinfectant as these tend to be irritating to the eye. Additionally, the surface active agents must not inhibit the wetting or conditioning function of the solution.

There is, therefore, a need for a composition with improved antibacterial and antibiofilm properties while maintaining or increasing the biocidal efficacy of the product without adversely affecting comfort or safety in terms of the level of toxicity to eye tissue. It is also desirable to have a composition that can be utilized as an eye drop, an eyewash solution, a contact lens care solution or a cleaning solution, a storing solution, a disinfectant, a cleaning-storing solution, and a cleaning disinfecting-storing solution.

Pedicure, manicure, and podiatry instruments, such as those for cleaning and scrubbing the feet and hands and containers for soaking the feet and hands, are typically reused many times for many different clients. To prevent the spread of bacteria and fungus, biocides, including antibacterials and antibiofilm solutions must be strong enough to be effective against a wide variety of bacteria, without adversely affecting comfort or safety of the client and the podiatrist or manicurist, in terms of the level of toxicity.

SUMMARY OF THE INVENTION

The instant invention may provide compositions and methods for prevention, decontamination or treatment of personal care products, including eye drops, eyewash solution, contact lens care solution, contact lens cleaning solution, contact lens storing solution, contact lens disinfectant, contact lens cleaning-storing solution, and contact lens cleaning disinfecting-storing solution, contact lens containers, contact lenses, as well as podiatric, manicure and pedicure solutions, gels, creams, jellies, powders, pastes, lotions, soaps and cleaners.

One embodiment of the invention may provide a composition comprising (a) one or more chelating agents, and (b) one or two metal ion salts.

In another embodiment, a composition of the invention comprises: (a) a small amount of at least two chelating agents, (b) a small amount of at least one metal ion salt, wherein the amount of each of components (a) and (b) is sufficient to form an effective anti-infective composition against bacterial infections in the personal care products.

In yet another embodiment, a composition of the invention comprises: (a) a small amount of at least two chelating agents, (b) a small amount of at least one metal ion salt, and (c) personal care acceptable excipients.

Still another embodiment of the invention may provide an anti-infective composition comprising two chelating agents and one or two metal ion salts that are effective against bacteria and fungi causing infections through the personal care products.

The compositions of the invention may be for use against one or more infection-associated bacteria or yeasts selected from the group consisting of *Methicillin*-resistant *Staphylococcus aureus* (MRSA), *Staphylococcus epidermidis*, *Coagulase* negative *staphylococci* (CoNS), *Vancomycin* resistant *Enterococci* (VRE), *Carbapenem* resistant *Klebsiella pneumoniae*, *Pseudomonas aeruginosa*, *Acinetobacter baumannii*, *Methicillin* resistant *Staphylococcus pseudintermedius* (MRSP), *Malassezia pachydermatis*, *Salmonella typhimurium*, *Escherichia coli* O157:H7, *Candida albicans*, *Listeria monocytogenes*, *Campylobacter jejuni*, *Bacillus* spp., *Streptococcus agalactiae*, *Streptococcus uberis*, *Esherichia coli*, *Salmonella choleraesuis*, *Stenotrophomonas maltophilia*, *Enterococcus faecalis*, *Proteus mirabilis*, *Klebsiella* spp., *Enterobacter* spp., and *Citrobacter* spp.

A further embodiment of the invention may provide an anti-infective composition comprising at least two chelating agents and one are two metal ion salts that are for use against bacteria and yeasts found in or with the personal care products.

In an embodiment, the chelating agent is between about 5000 mg/L and about 50000/L of the composition. In an embodiment, the metal ion salt is between about 1000 mg/L and about 10000 mg/L of the composition.

The chelating agents may be selected from the group consisting of EDTA, EGTA, DTPA, EDDHA, IDA, CDTA, HEDTA, HEIDA, NTA, sodium citrate, potassium citrate, ovotransferrin and lactoferrin. The metal ion salts may be selected from the group consisting of zinc chloride, zinc lactate, zinc citrate, zinc gluconate, zinc sulfate zinc acetate, silver ion or silver sulfadiazine, silver sulfate, silver nitrate, and silver carbonate.

In another embodiment, the chelating agents are EDTA and sodium citrate, and metal ion salt is zinc chloride or zinc sulfate. The EDTA may be present at about 10 mg/ml and sodium citrate may be present at about 10 mg/ml. The zinc chloride or zinc lactate may be present at about 1 mg/ml.

The composition may further comprise one or more ingredients selected from the group consisting of: water, citrate buffer, citric acid, stabilizing agent, a flavoring agent, vitamins, minerals, herbals, a surfactant, an antimicrobial peptide, an antimicrobial and a pH adjuster. The antimicrobial preservatives can be selected from potassium sorbate, potassium benzoate, sodium benzoate and benzoic acid, and can, in particular be used in contact lens cleaning and disinfecting solutions. The antimicrobial preservative can be in a concentration ranging from 0.25 g/L to 3 g/L.

The invention may also teach methods of preparing a suitable formulation for use with the personal care products in a variety of ways, for example in a disinfecting solution, a lotion, cream, a gel, a spray, a thermoreversible gel spray, and a paste.

The invention further may teach methods of preparing suitable formulations for treating or impregnating personal care products, including contact lenses, contact lens containers, and manicure, pedicure and podiatry tools and containers.

The formulations can also include natural or synthetic flavorings and coloring agents. Thickening agents can also be added to compositions of the invention such as guar gum, carbopol, polyethylene glycol, pluronic F-127, sodium alginate, carboxymethyl cellulose, xanthan gum and other personal care acceptable thickening agents.

Other formulations will be readily apparent to one skilled in the art. A composition of the invention can include antibiofilm enzymes (cellulase, beta-N-acetylgluconase, DispersinB, papain, DNase 1, etc.), antimicrobial peptides, antibiotics (gentamicin, ciprofloxacin, ampicillin, cefamandole nafate, rifambicin, etc.), antimicrobials (triclosan, chlorhexidine, quaternary ammonium compounds, silver, silver salts, etc.) and other antibiofilm compounds.

The invention may also teach the use of liposomal or nanoparticle delivery systems that enhance the stability and efficacy of anti-infective compounds in the compositions.

The invention may also teach personal care products treated or impregnated with a composition of the invention, such as a contact lens, a contact lens container, a hand washing container, a hand or foot scrubber, and a foot washing container.

DETAILED DESCRIPTION OF THE INVENTION

Definitions

Figure 1:
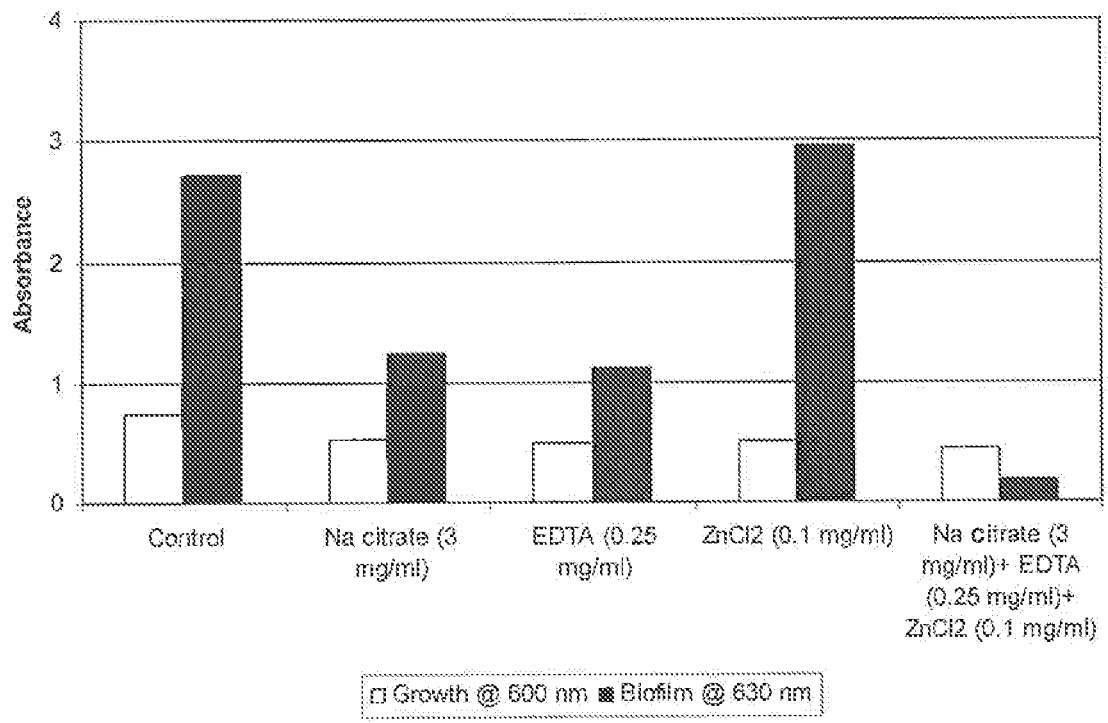
FIG. 1 is a bar graph showing the inhibitory effect of sodium citrate (3 mg/ml), EDTA (0.25 mg/ml) and $ZnCl_2$ (0.1 mg/ml) alone and in combination on methicillin-resistant *Staphylococcus aureus* (MRSA) growth and biofilm formation

The term "antimicrobial" refers to a compound or a composition that kills or inhibits or stops the growth of microorganisms, including, but not limited to bacteria and yeasts.

The term "biofilm" refers to a structured community of microorganisms enclosed in a self produced extracellular polymeric matrix, and attached to a biotic or abiotic surface. Bacteria in a biofilm can be 1000 times more resistant to antibiotics/antimicrobials compared to their planktonic (free living) counterparts.

The term "biofilm formation" refers to the attachment of microorganisms to surfaces and the subsequent development of multiple layers of cells.

The term "antibiofilm" refers to inhibition of microbial biofilm formation and disruption or dispersal of preformed biofilms.

The term "infection" refers to the invasion and multiplication of microorganisms such as bacteria, viruses, and parasites that are not normally present within the body. An infection may cause no symptoms and be subclinical, or it may cause symptoms and be clinically apparent. Microorganisms that live naturally in the body are not considered infections.

The term "personal care product" refers to ophthalmic products, including eye drops, eyewash solution, contact lens care solution, contact lens cleaning solution, contact lens storing solution, contact lens disinfectant, contact lens cleaning-storing solution, and contact lens cleaning disinfecting-storing solution, contact lens containers, contact lenses, as well as podiatric, manicure and pedicure solutions, gels, creams, jellies, powders, pastes, lotions, soaps and cleaners, as well as hand washing containers, hand and foot scrubbers, cuticle soaking solutions, and foot washing containers.

The term "disinfectants" refers to substances that are applied to non-living objects to destroy microorganisms that are living on the objects. Disinfection does not necessarily kill all microorganisms, especially resistant bacterial spores; it is less effective than sterilization, which is an extreme physical and/or chemical process that kills all types of life. Disinfectants are different from other antimicrobial agents such as antibiotics, which destroy microorganisms within the body, and antiseptics, which destroy microorganisms on living tissue. Disinfectants are also different from biocides—the latter are intended to destroy all forms of life, not just microorganisms. Disinfectants work by destroying the cell wall/membrane of microbes or interfering with metabolism and growth.

The term "inhibition" refers to at least a decrease of the personal care products-associated bacterial growth and biofilm formation.

The term "prevention" refers to at least preventing a condition associated with bacteria occurring in a mammal, particularly when the mammal is found to be predisposed to having the condition but has not yet been diagnosed as having it.

A "preventative amount" as used herein includes a prophylactic amount, for example, an amount effective for preventing or protecting a the personal care products. By administering a peptide suitable for use in methods of the invention concurrently with an antimicrobial, the peptide and/or the antimicrobial may be administered in a dosage amount that is less than the dosage amount required when the antimicrobial is administered as a sole active ingredient. By administering lower dosage amounts of active ingredient, side effects associated therewith could be reduced.

The term "metal ion salt" refers to salt of a metal ion such as zinc chloride, zinc lactate, zinc citrate, zinc gluconate, zinc sulfate zinc acetate, silver ion or silver sulfadiazine, silver sulfate, silver nitrate, and silver carbonate.

The present invention may teach anti-infective compositions offering antimicrobials and antibiofilm activity, containing combinations of chelating agents with other antimicrobial agents, such as, for example, antimicrobials/antibiofilm compounds, metal ion salts with gelling agents, surfactants or stabilizing agents.

Novel compositions that combine chelating agents together with metal ion salts such that lesser quantities of chelating agents and/or metal ion salts than would normally be necessary for an antimicrobial composition are used to achieve significant bacterial growth and biofilm inhibition. Higher concentrations of these compounds can be used if it is desired for certain applications.

The amount of chelating agents to be used in the antimicrobial composition of this invention can be between 10000 to 100000 mg/L. The higher end of this stated range might be used to prepare a concentrated product that would be diluted prior to use. For non-concentrated products, the amount of to be used in this invention is preferably between about 5000 to 10000 mg/L. Preferably, the range is between about 1000 to 5000 mg/L.

The amount of chelating agents to be used should be between about 1000 to 5000 mg/L. The higher end of this range might apply if the compositions were formulated as a concentrate. For non-concentrated products, the amount of chelating agent to be used in this invention is preferably between about 500 to 5000 mg/L. Preferably, the range is between about 1000 to 3000 mg/L, more preferably between about 2000 to 3000 mg/L.

For less concentrated solutions, such as for opthalmic use, the disodium EDTA may be between about 10 mg/L-50 mg/L of the composition, sodium citrate may be between about 100 mg/L-500 mg/L of the composition, and zinc chloride or zinc citrate may be between about 1 mg/L-10 mg/L.

Preparation

By one method, if a two-component composition is formed containing one or two chelating agents and a metal ion salt, these compounds can be combined in the following manner: With good stirring, a chelating agent can be dissolved in water, followed by a metal ion salt. It should be noted, however, that the addition order can be reversed.

Additionally, antimicrobials/antimicrobial peptides, antibiotics, antibiofilm compounds, quaternary ammonium compounds and surfactants also may be advantageously combined with chelating agents in an antimicrobial composition. A composition of the invention comprises: (a) a small amount of at least one or two chelating agent; (b) a small amount of a metal ion salt or iron-sequestering glycoprotein or antimicrobial peptide or an antibiotic or an antibiofilm compound; and (c) a sparing amount of at least one compound from the group consisting of a stabilizing agent and/or a gelling agent and/or a surfactant, wherein, the amount of each of component (a), (b) and (c) is sufficient to form, in combination, an effective anti-infective composition for the personal care products.

The concentration of active components in the compositions may vary as desired or necessary to decrease the amount of time the composition of the invention is used for the personal care products. These variations in active components concentration are easily determined by persons skilled in the art.

Compositions

The present invention may include unique and enhanced anti-infective compositions for the personal care products comprising at least two chelating agents and one metal ion salt.

In an embodiment, two chelating agents and a metal ion salt containing composition includes an antimicrobial compound. The chelating agents and a metal ion salt containing composition with an antimicrobial and/antibiofilm compound has an enhanced inhibitory effect on the personal care products-associated bacterial growth and biofilm formation. In an embodiment of the invention, an enhanced antimicrobial-antibiofilm composition comprises at least one or two chelating agents, one metal ion salt and one or more antimicrobial agents comprising antiseptics (e.g., triclosan, chlorhexidine salt, cetylpyridinium chloride, etc.), antibiotics and bacteriocins (e.g., nisin, epidermin, gallidennin, cinnamycin, duramycin, lacticin 481, etc.), and iron-sequestering glycoproteins (ovotransferrin, lactoferrin and serrotransferrin). Additionally, the personal care product compositions may comprise ingredients such as citrate (e.g., citric acid, zinc citrate, sodium citrate, potassium citrate, etc.), minerals (e.g., mineral salts such as zinc chloride, zinc gluconate, zinc lactate, zinc citrate, zinc sulfate, zinc acetate, silver, silver sulfate, silver sulfadiazine, silver nitrate, silver carbonate, etc.), and triterpenoids (e.g., oleanolic acid and ursolic acid) and chitosan.

In an embodiment, a composition comprises an antibiotic and one or two chelating agents and also one metal ion salt. Antibiotics are well known. Groups of antibiotics include, but are not limited to, β-lactam inhibitors (e.g., penicillin, ampicillin, amoxicillin, methicillin, etc.), cephalosporins (e.g., cephalothin, cephamycin, etc.), aminoglycosides (e.g., streptomycin, tobramycin, etc.), polyenes (e.g., amphotericin, nystatin, etc.), macrolides (e.g., erythromycin, etc.), tetracyclines (e.g., tetracycline, doxycycline, etc.), nitroimidazole (e.g., metronidazole), quinolones (e.g., nalidixic acid), rifamycins (e.g., rifampin), and sulfonamides (e.g., sulfanilamide), nitroaromatics (e.g., chloramphenicol) and pyridines (e.g., isoniazid).

In an embodiment, a composition comprises an antiseptic, one or two chelating agents and one metal ion salt. Antiseptics are agents that kill or inhibit the growth of microorganisms on the external surfaces of the body. Antiseptics include, but are not limited to, triclosan, chlorhexidine salt, and cetylpyridinium chloride.

In an embodiment, a composition comprises an antibiofilm compound, one or two chelating agents and a metal ion salt. Antibiofilm compounds include, but not limited to, DisperinB, DNase I, Proteinase K, apyrase, cis-2-decenoic acid, alginate lyase, lactoferrin, gallium, cellulase, and 5-fluorouracil.

In an embodiment, a composition is effective for inhibiting growth and biofilm formation in the personal care products. The composition is also effective in disrupting or dispersing preformed biofilms, which makes biofilm-embedded bacteria more susceptible to antimicrobial killing. Under appropriate environmental conditions, such as moisture and pH, infections can be modulated using embodiments of the invention.

An embodiment of the invention may also include other personal care acceptable vehicles, diluents, and additives such as antioxidants, anti-inflammatory compounds, vitamins, tissue degrading enzymes, buffers and solutes that render the formulation isotonic in the intended recipient; and aqueous and non-aqueous sterile suspensions which may include suspending agents, surfactants and thickening agents.

Personal Care Formulations

A composition of the invention may be added to a variety of formulations suitable for applying/delivering the composition to the personal care products, including, but not limited to, disinfecting solutions, lotions, creams, gels, sprays. To provide such formulations, a composition of this invention is combined with one or more personal care acceptable excipients.

Formulations including, but not limited to, personal care acceptable compositions comprising one or two chelating agents and a metal ion salt in combination with an antiseptic, an antibiotic, an antimicrobial, an iron-sequestering glycoprotein, a bacteriocin, extracellular matrix or chitosan can be prepared by any known method.

In general, methods of manufacturing anti-infective compositions may comprise combining a personal care acceptable carrier and an effective amount of both chelating agents and a metal ion salt with an antiseptic, an antibiotic, a bacteriocin, an antimicrobial peptide or chitosan.

A variety of carriers and excipients can be used to formulate an embodiment of this invention and are well known. Such personal care acceptable vehicles include, but are not limited to, water, ethanol, humectants such as polypropylene glycol, glycerol and sorbitol, gelling agents such as cellulose derivatives, polyoxypropylene/polyoxyethylene block copolymers, carboxy methyl cellulose, pluronic F-127, sodium alginate, polyethylene glycol, thickening agents such as Carbopol™ 934.

Method of Treatment

For use in treating or disinfecting personal care products, preferred concentration range of ingredients may include:
(i) Sodium Citrate: (a) 50,000 mg/L-100,000 mg/L, (b) 25,000 mg/L-50,000 mg/L, (c) 10,000 mg/L-25,000 mg/L, (d) 5,000 mg/L-10,000 mg/L, & (e) 1,000 mg/L-5,000 mg/L.
(ii) Disodium EDTA: (a) 10,000 mg/L-25,000 mg/L, (b) 5,000 mg/L-10,000 mg/L, (c) 1,000 mg/L-5,000 mg/L, (d) 500 mg/L-1,000 mg/L, & (e) 100 mg/L-500 mg/L
(iii) Zinc Chloride: (a) 1,000 mg/L-5,000 mg/L, (b) 500 mg/L-1,000 mg/L, (c) 100 mg/L-500 mg/L, and (d) 10 mg/L-100 mg/L.

In one embodiment, one or more chelating agents and a metal ion salt together is formulated as personal care acceptable medicament as described herein comprising a carrier and an effective amount of composition comprising one or more chelating agents and a metal ion salt as active ingredients.

In a further embodiment of the invention, an enhanced personal care product does not present any antibiotic resistance concerns and bio-compatibility/safety issues. Also, the composition of this invention comprising one or two chelating agents (EDTA and sodium citrate) and a metal ion salt (zinc chloride or zinc sulfate or zinc lactate) has GRAS (Generally Recognized as Safe) status and all these ingredients are food as well as feed additives.

The present invention may be better understood with reference to the following examples. These examples are intended to be representative of specific embodiments of the invention, and are not intended as limiting the scope of the invention.

EXAMPLES

Example 1

Inhibitory Effect of Sodium Citrate, EDTA and Zinc Chloride Alone and in Combination on *Methicillin*-Resistant *Staphylococcus aureus* (MRSA) Growth and Biofilm Formation An overnight broth culture of *S. aureus* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 1).

Example 2

Figure 2:
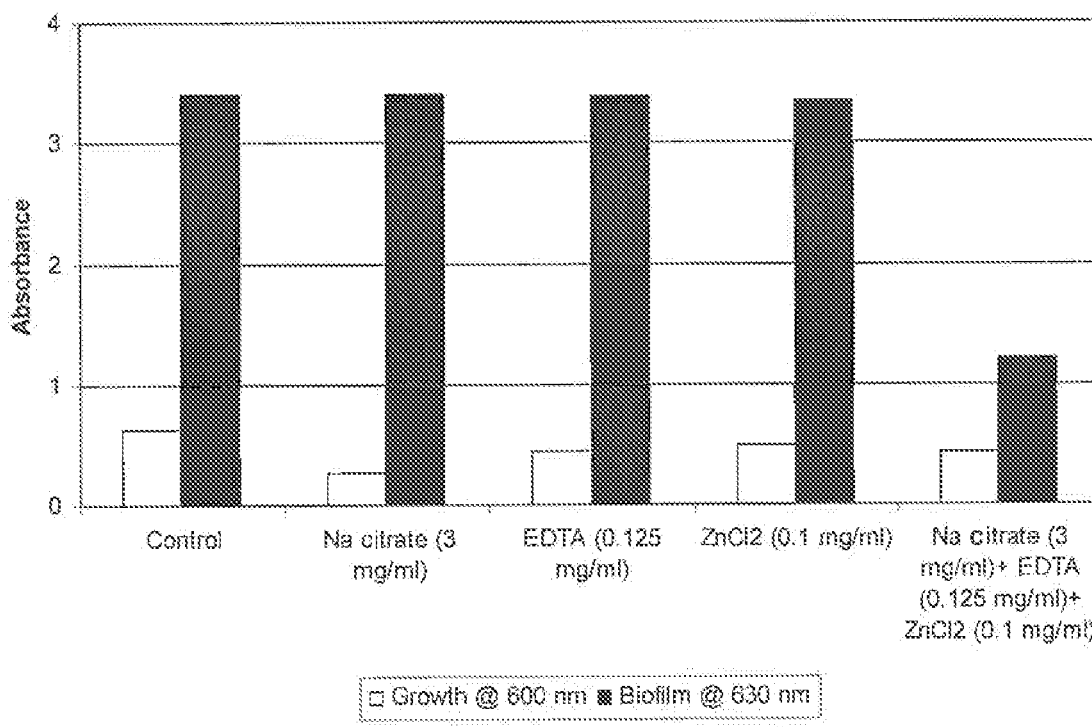
FIG. 2 is a bar graph showing the inhibitory effect of sodium citrate (3 mg/ml), EDTA (0.125 mg/ml) and $ZnCl_2$ (0.1 mg/ml) alone and in combination on methicillin-resistant *Staphylococcus pseudintermedius* (MRSP) growth and biofilm formation

Inhibitory Effect of Sodium Citrate, EDTA and Zinc Chloride Alone, and in Combination on *Methicillin*-Resistant *Staphylococcus Pseudintermedius* (MRSP) Growth and Biofilm Formation An overnight broth culture of methicillin resistant *S. pseudintermedius* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 2).

Example 3

Figure 3:
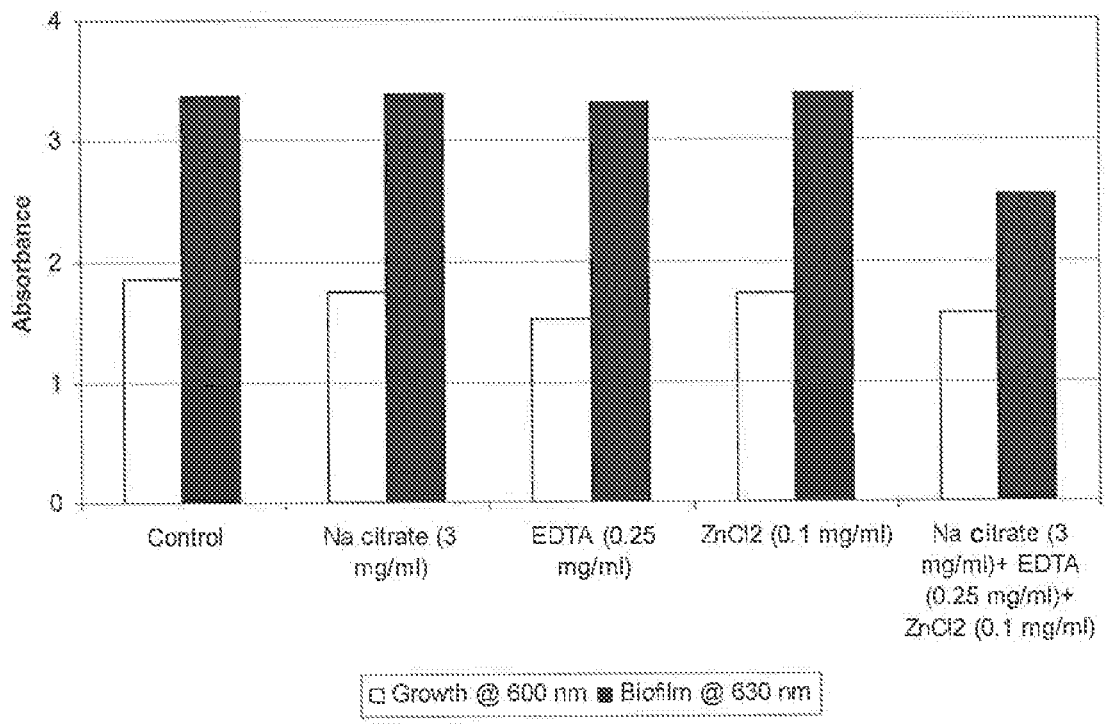
FIG. 3 is a bar graph showing the inhibitory effect of sodium citrate (3 mg/ml), EDTA (0.25 mg/ml) and $ZnCl_2$ (0.1 mg/ml) alone and in combination on *Pseudomonas aeruginosa* growth and biofilm formation

Inhibitory Effect of Sodium Citrate, EDTA, and Zinc Chloride Alone, and in Combination on *Pseudomonas aeruginosa* Growth and Biofilm Formation An overnight broth culture of *P. aeruginosa* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 3).

Example 4

Figure 4:
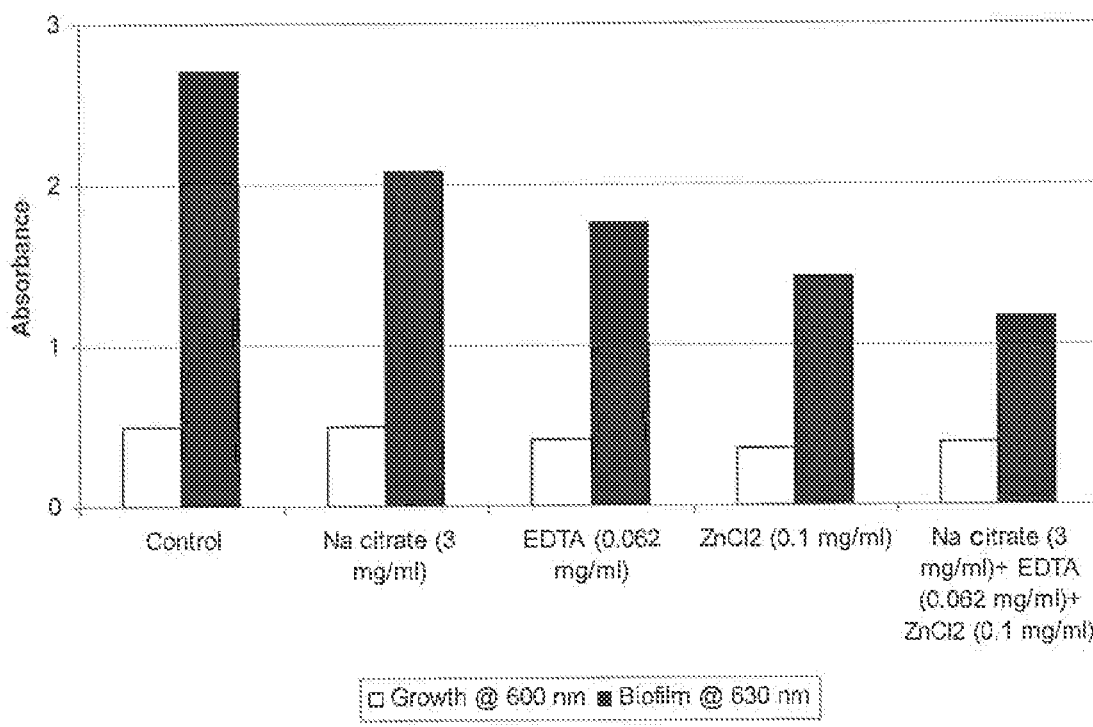
FIG. 4 is a bar graph showing the inhibitory effect of sodium citrate (3 mg/ml), EDTA (0.062 mg/ml) and $ZnCl_2$ (0.1 mg/ml) alone and in combination on *Listeria monocytogenes* growth and biofilm formation

Inhibitory Effect of Sodium Citrate, EDTA, and Zinc Chloride Alone and in Combination on *Listeria monocytogenes* Growth and Biofilm Formation An overnight broth culture of *L. monocytogenes* was grown in TSB and used as inoculum. 96-well microplates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition, comprising sodium citrate, EDTA and zinc chloride showed an enhanced inhibitory effect on biofilm formation, as compared to sodium citrate, or EDTA, or zinc chloride alone (FIG. 4).

Example 5

Figure 5:
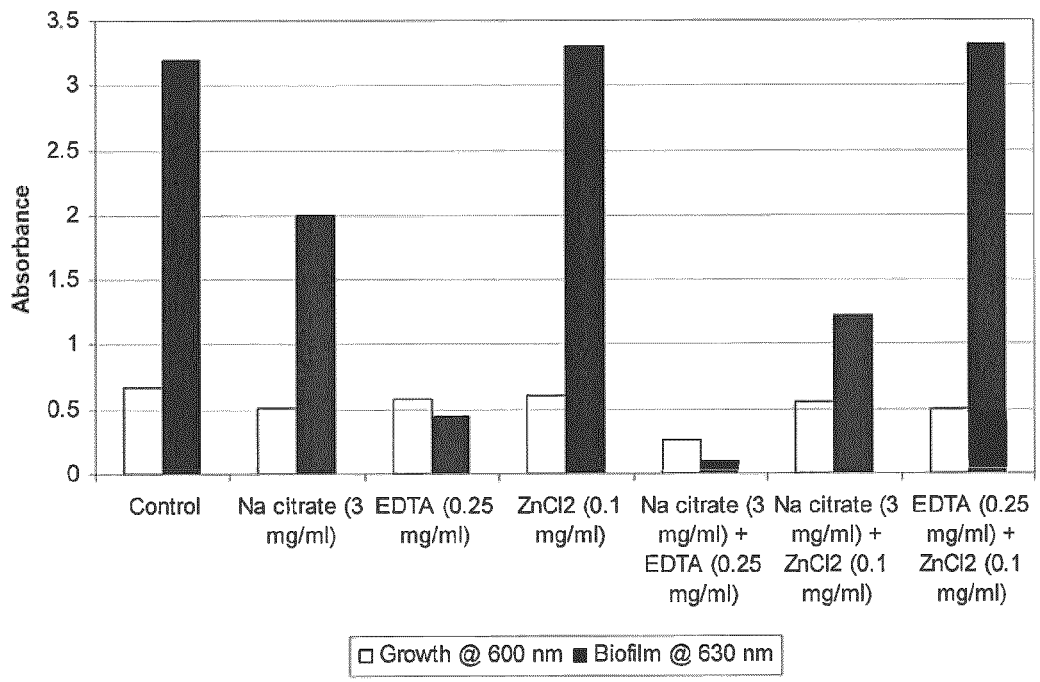
FIG. 5 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$ and EDTA+$ZnCl_2$ combinations on methicillin-resistant *Staphylococcus aureus* (MRSA) growth and biofilm formation

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on Methicillin-Resistant Staphylococcus aureus [MRSA] Growth and Biofilm Formation An overnight broth culture of S. aureus (MRSA) was grown in TSB and used as inoculum. 96-well microplates containing TSB in the absence and the presence of each compound (sodium citrate or EDTA or Zinc chloride) separately and Sodium citrate+EDTA, Sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA and Sodium citrate+$ZnCl_2$ combinations showed an enhanced inhibitory effect on biofilm formation, as compared to sodium citrate, or EDTA, or zinc chloride alone (FIG. 5).

Example 6

Figure 6:
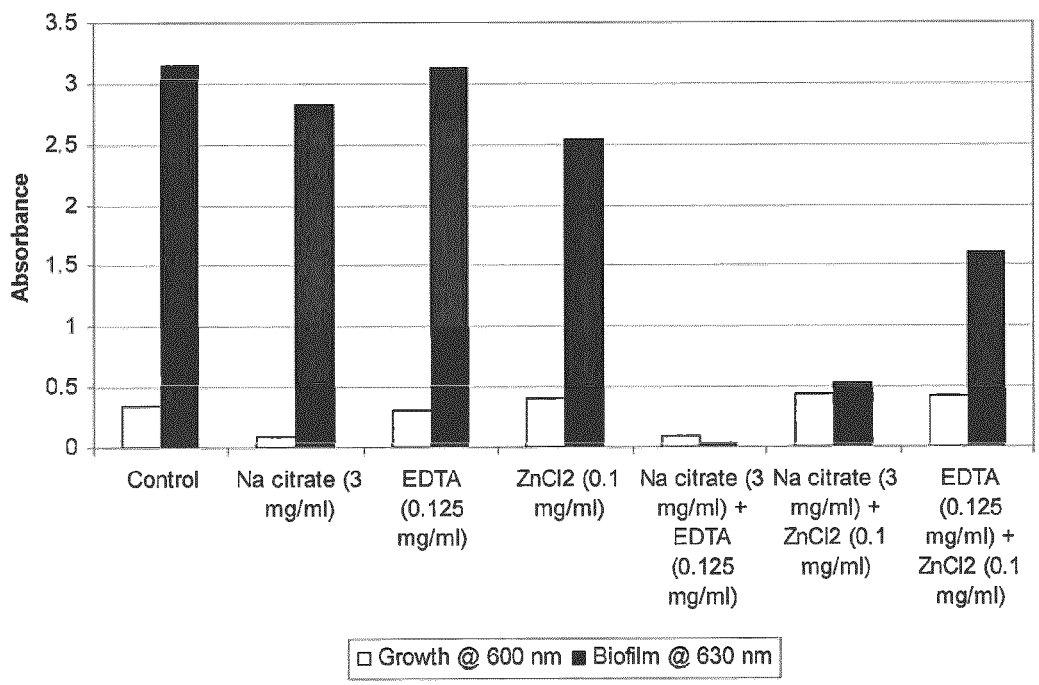
FIG. 6 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on methicillin-resistant *Staphylococcus pseudintermedius* (MRSP) growth and biofilm formation

Effect of Sodium Citrate, EDTA, and $ZnCl_2$ Alone, and Sodium Citrate+EDTA, Sodium Citrate+$ZnCl_2$, and EDTA+$ZnCl_2$ Combinations on Methicillin Resistant Staphylococcus pseudintermedius (MRSP) Growth and Biofilm Formation An overnight broth culture of MRSP was grown in TSB and used as inoculum. 96-well microplates containing TSB in the absence and the presence of each compound (sodium citrate or EDTA or Zinc chloride) separately and Sodium citrate+EDTA, Sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, Sodium citrate+$ZnCl_2$, and EDTA+$ZnCl_2$ combinations showed an enhanced inhibitory effect on biofilm formation, as compared to sodium citrate, or EDTA, or zinc chloride alone (FIG. 6).

Example 7

Figure 7:
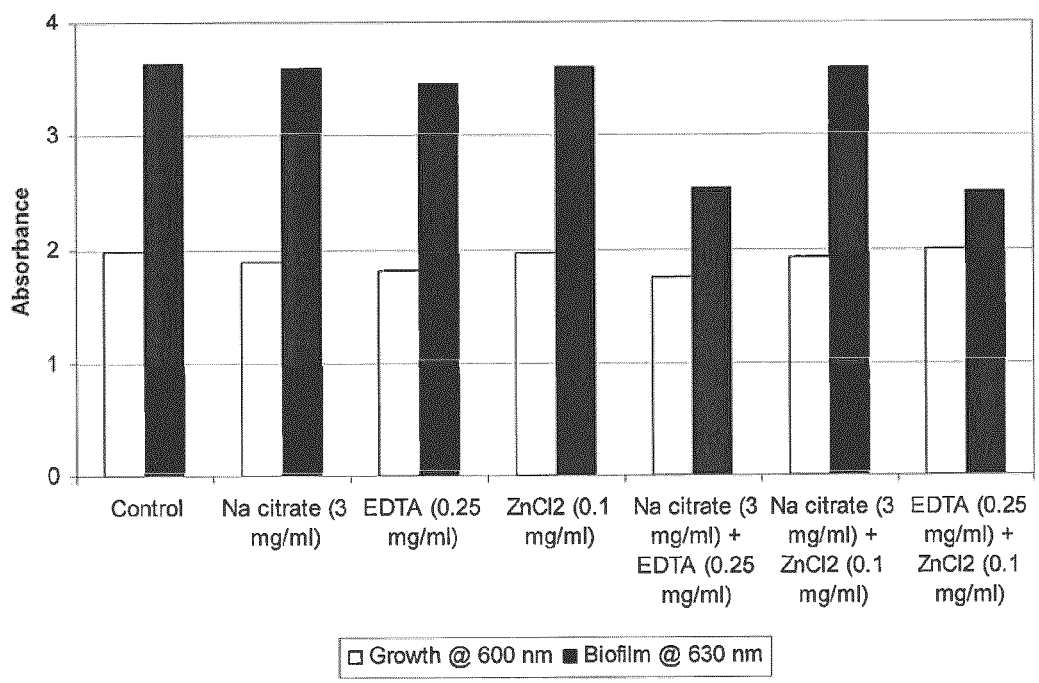
FIG. 7 is a bar graph showing the inhibitory effect of sodium citrate (3 mg/ml), EDTA (0.25 mg/ml), and $ZnCl_2$ (0.1 mg/ml) alone, and sodium citrate+EDTA, sodium citrate+$ZnCl_2$, and EDTA+$ZnCl_2$ combinations on *Pseudomonas aeruginosa* growth and biofilm formation

Inhibitory Effect of Sodium Citrate, EDTA, and $ZnCl_2$ Alone, and Sodium Citrate+EDTA, Sodium Citrate+$ZnCl_2$, and EDTA+$ZnCl_2$ Combinations on Pseudomonas aeruginosa Growth and Biofilm Formation An overnight broth culture of P. aeruginosa was grown in TSB and used as inoculum. 96-well microplates containing TSB in the absence and the presence of each compound (sodium citrate or EDTA or Zinc chloride) separately and Sodium citrate+EDTA, Sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, and EDTA+$ZnCl_2$ combinations showed an enhanced inhibitory effect on biofilm formation, as compared to sodium citrate, or EDTA, or zinc chloride alone (FIG. 7).

Example 8

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on Salmonella choleraesuis ATCC 10708

Figure 8:
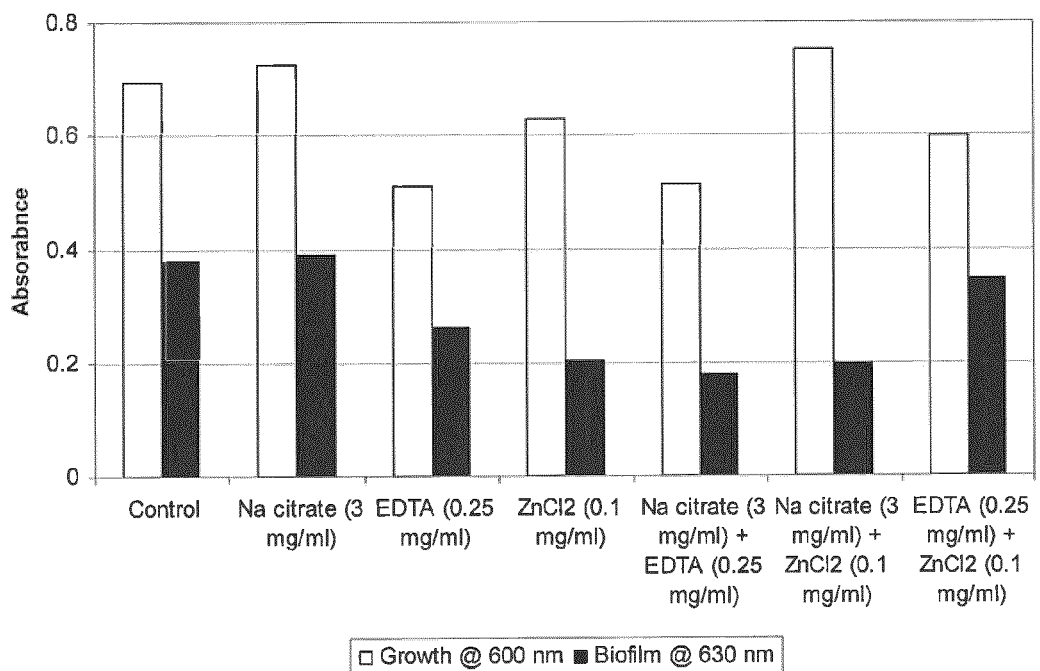
FIG. 8 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Salmonella choleraesuis* ATCC 10708 growth and biofilm formation

An overnight broth culture of S. choleraesuis ATCC 10708 was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 8).

Example 9

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on Escherichia coli O157:H7

Figure 9:
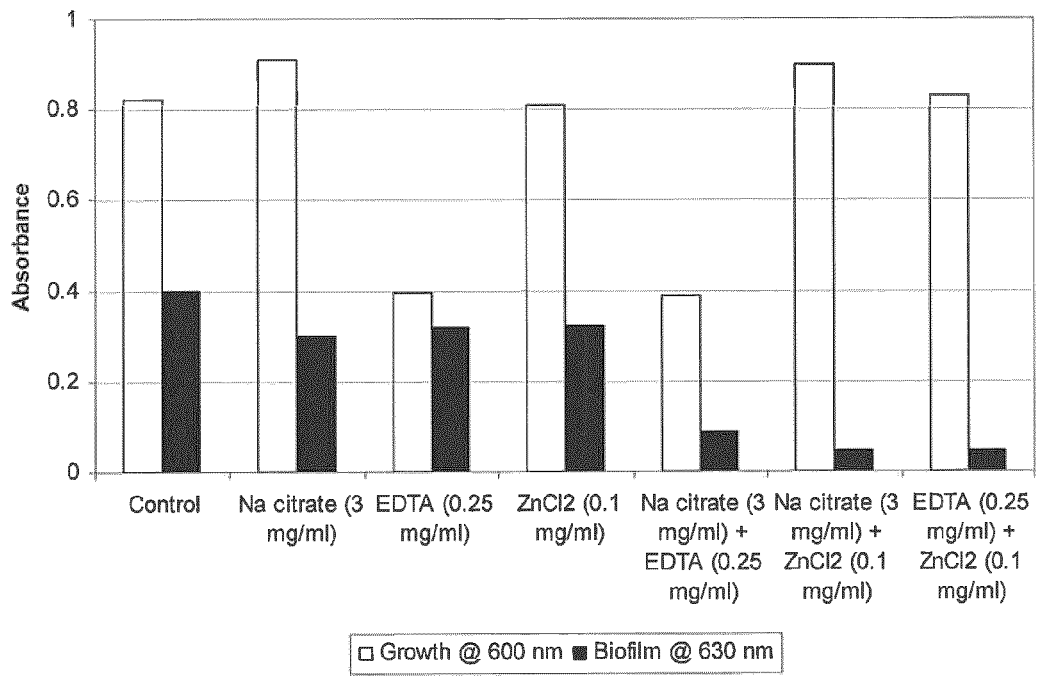
FIG. 9 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Escherichia coli* O157:H7 growth and biofilm formation

An overnight broth culture of E. coli O157:H7 was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, Sodium citrate+ZnCl2, and EDTA+ZnCl2 combinations showed an enhanced inhibitory effect on biofilm formation, as compared to sodium citrate, or EDTA or zinc chloride alone (FIG. 9).

Example 10

Inhibitory Effect of Sodium Citrate, EDTA and $ZnCl_2$ Alone, and in Combination on Escherichia coli O157:H7

Figure 10:
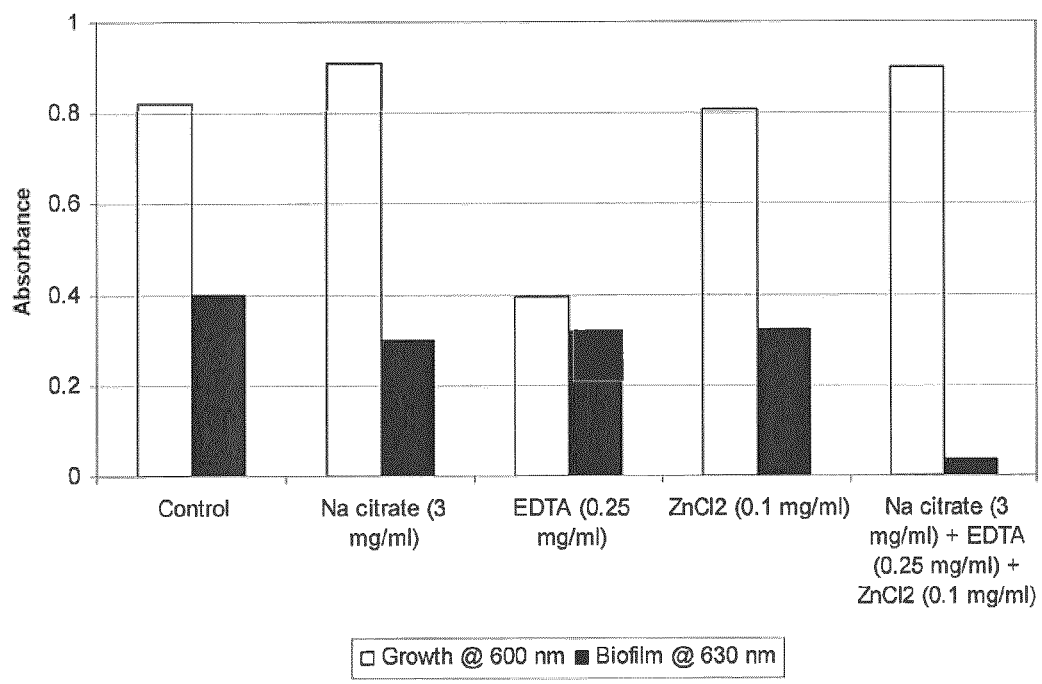
FIG. 10 is a bar graph showing the inhibitory effect of sodium citrate (3 mg/ml), EDTA (0.25 mg/ml) and $ZnCl_2$ (0.1 mg/ml) alone, and in combination on *Escherichia coli* O157:H7 growth and biofilm formation

An overnight broth culture of E. coli O157:H7 was grown in TSB and used as inoculum. 96-well microtiter plates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising sodium citrate, EDTA, and $ZnCl_2$ showed an enhanced inhibitory effect on biofilm formation, as compared to sodium citrate, or EDTA, or zinc chloride alone (FIG. 10).

Example 11

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Staphylococcus epidermidis*

Figure 11:
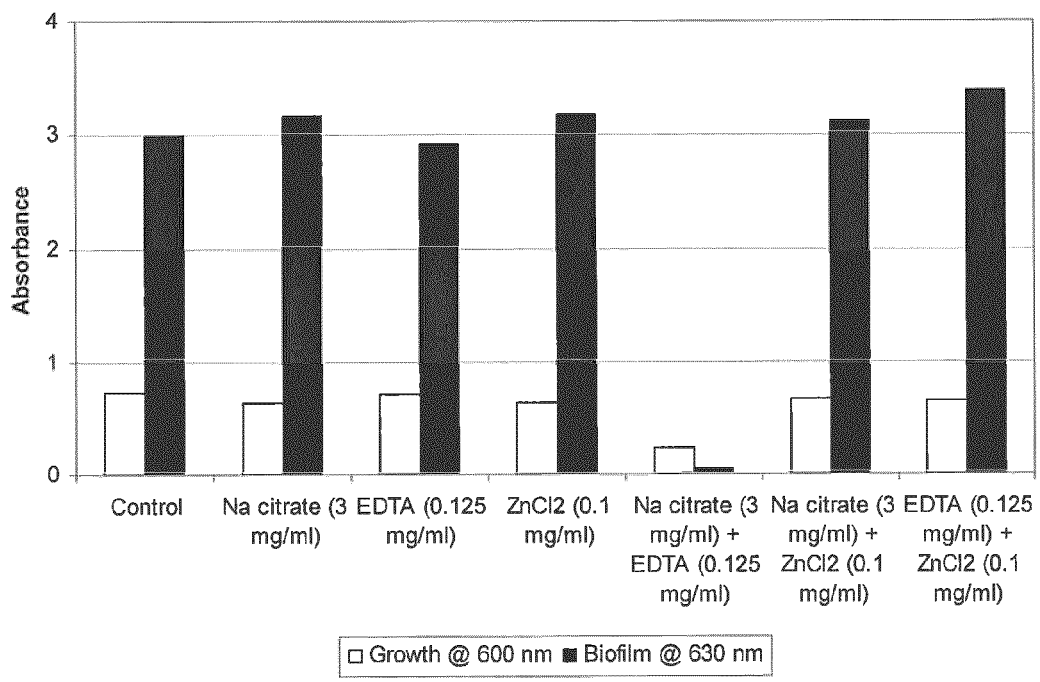
FIG. 11 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on *Staphylococcus epidermidis* growth and biofilm formation

An overnight broth culture of *S. epidermidis* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 11).

Example 12

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Coagulase*-Negative *Staphylococci* (CoNS-42)

Figure 12:
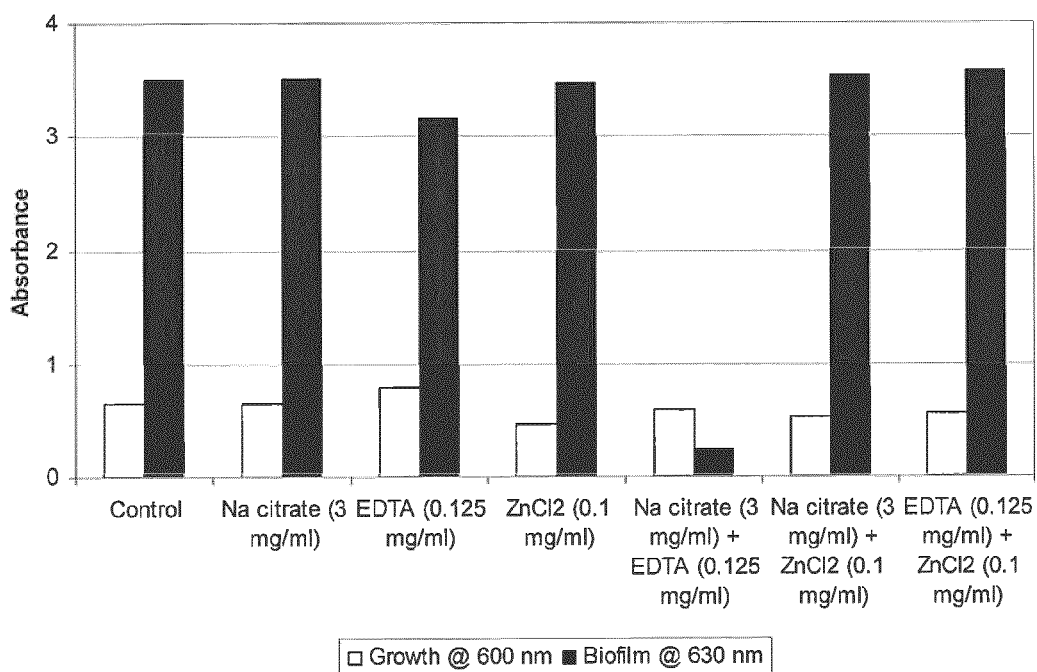
FIG. 12 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on Coagulase-negative *Staphylococci* (CoNS-42) growth and biofilm formation

An overnight broth culture of CoNS-42 was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 12).

Example 13

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Streptococcus agalactiae* ATCC 12386

Figure 13:
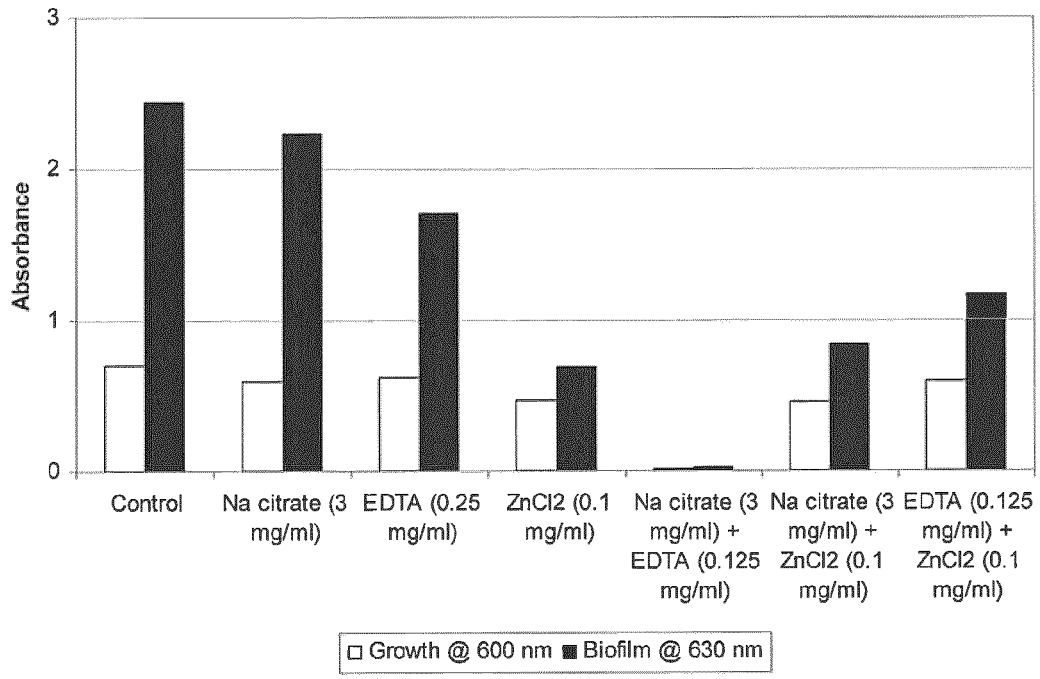
FIG. 13 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Streptococcus agalactiae* ATCC 12386 growth and biofilm formation

An overnight broth culture of *S. agalactiae* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 13).

Example 14

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Klebsiella pneumoniae*

Figure 14:
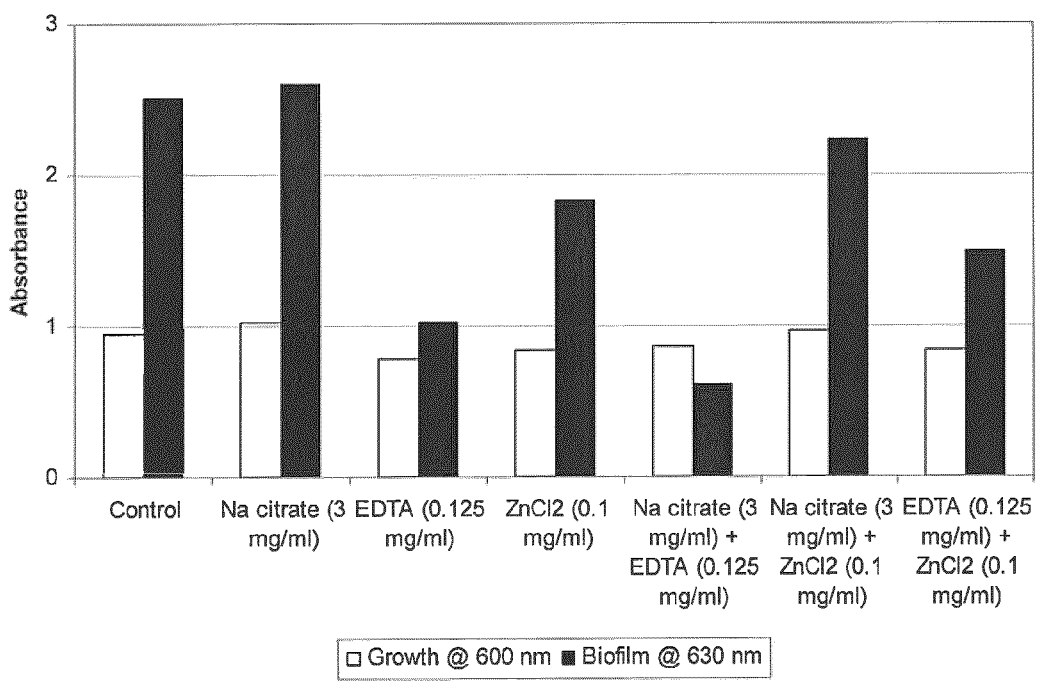
FIG. 14 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on *Klebsiella pneumoniae* growth and biofilm formation

An overnight broth culture of *K. pneumoniae* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 14).

Example 15

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Acinetobacter baumannii*

Figure 15:
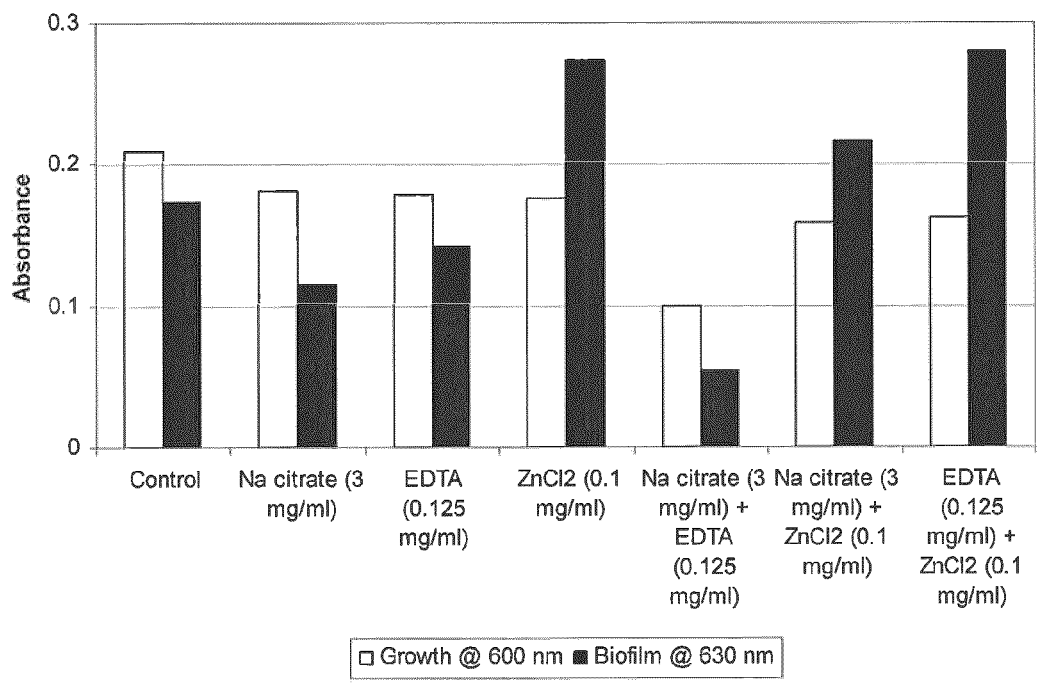
FIG. 15 is a bar graph showing the inhibitory effect of sodium citrate (3 mg/ml), EDTA (0.125 mg/ml) and $ZnCl_2$ (0.1 mg/ml) alone, and sodium citrate+EDTA, sodium citrate+$ZnCl_2$, and EDTA+$ZnCl_2$ combinations on *Acinetobacter baumannii* growth and biofilm formation

An overnight broth culture of *A. baumannii* was grown in TSB and used as inoculum. 96-well microtiter plates containing TSB in the absence and the presence of each compound (sodium citrate or EDTA or Zinc chloride) separately and sodium citrate+EDTA, sodium citrate+$ZnCl_2$, and EDTA+$ZnCl_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 15).

Example 16

Inhibitory Effect of Sodium Citrate, EDTA and $ZnCl_2$ Alone, and Sodium Citrate+EDTA, Sodium Citrate+$ZnCl_2$, and EDTA+$ZnCl_2$ Combinations on *Stenotrophomonas maltophilia*

Figure 16:
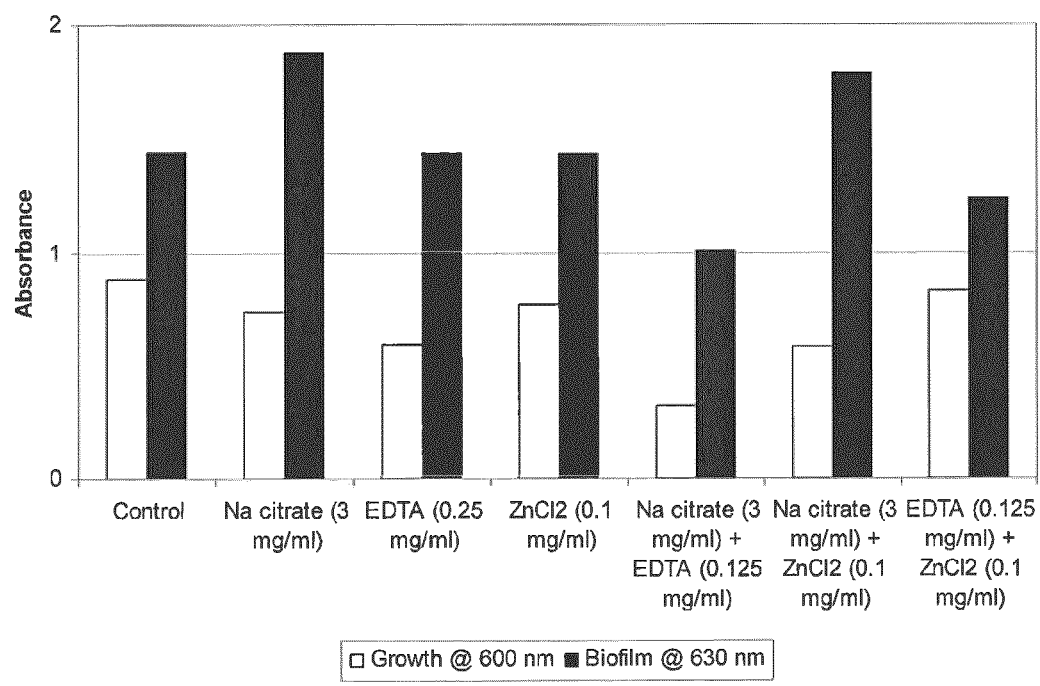
FIG. 16 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Stenotrophomonas maltophilia* growth and biofilm formation

An overnight broth culture of *S. maltophilia* was grown in TSB and used as inoculum. 96-well microtiter plates containing TSB in the absence and the presence of each compound (sodium citrate or EDTA or Zinc chloride) separately and sodium citrate+EDTA, sodium citrate+ZnCl$_2$, and EDTA+ZnCl$_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 16).

Example 17

Inhibitory Effect of Sodium Citrate, EDTA and ZnCl$_2$ Alone, and Sodium Citrate+EDTA, Sodium Citrate+ZnCl$_2$, and EDTA+ZnCl$_2$ Combinations on *Vancomycin*-Resistant *Enterococci* (VRE)

Figure 17:
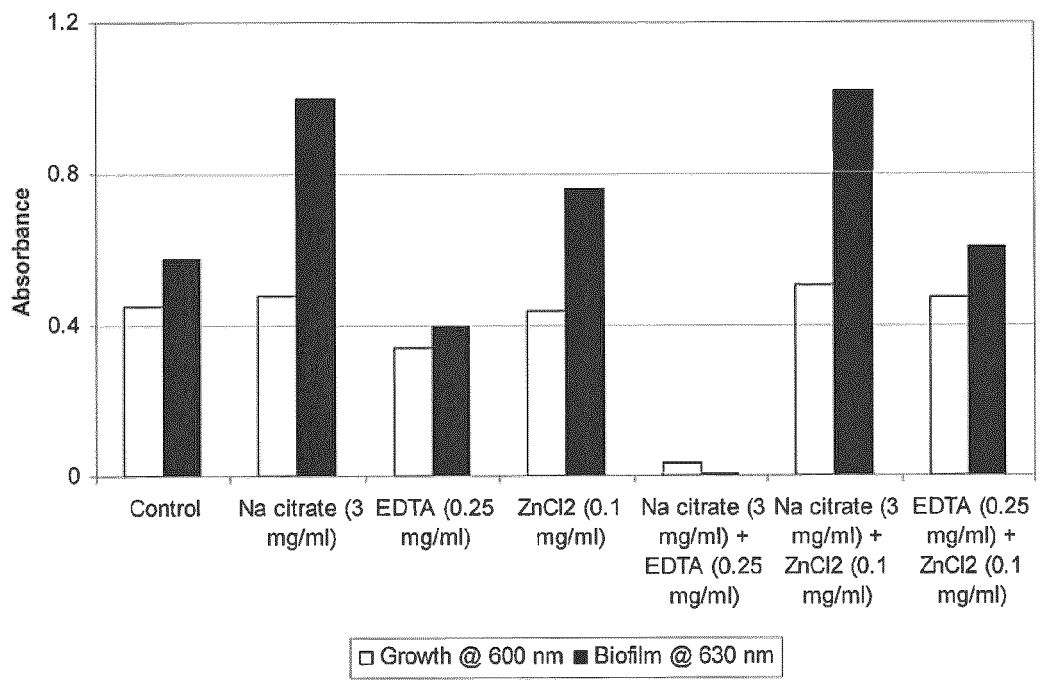
FIG. 17 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on Vancomycin-resistant *Enterococci* (VRE) growth and biofilm formation

An overnight broth culture of VRE was grown in TSB and used as inoculum. 96-well microtiter plates containing TSB in the absence and the presence of each compound (sodium citrate or EDTA or Zinc chloride) separately and sodium citrate+EDTA, sodium citrate+ZnCl$_2$, and EDTA+ZnCl$_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 17).

Example 18

Inhibitory Effect of Sodium Citrate, EDTA and ZnCl$_2$ Alone, and Sodium Citrate+EDTA, Sodium Citrate+ZnCl$_2$, and EDTA+ZnCl$_2$ Combinations on *Enterococcus faecalis*

Figure 18:
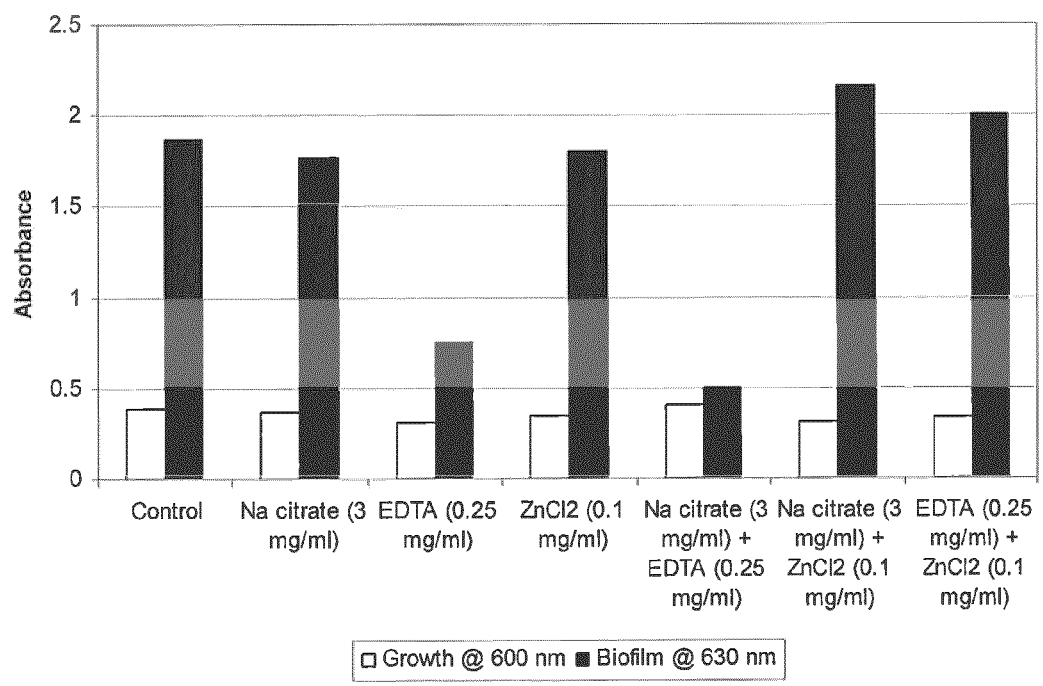
FIG. 18 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Enterococcus faecalis* growth and biofilm formation

An overnight broth culture of *E. faecalis* was grown in TSB and used as inoculum. 96-well microtiter plates containing TSB in the absence and the presence of each compound (sodium citrate or EDTA or Zinc chloride) separately and sodium citrate+EDTA, sodium citrate+ZnCl$_2$, and EDTA+ZnCl$_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 18).

Example 19

Inhibitory Effect of Sodium Citrate, EDTA and ZnCl$_2$ Alone, and Sodium Citrate+EDTA, Sodium Citrate+ZnCl$_2$, and EDTA+ZnCl$_2$ Combinations on *Proteus mirabilis*

Figure 19:
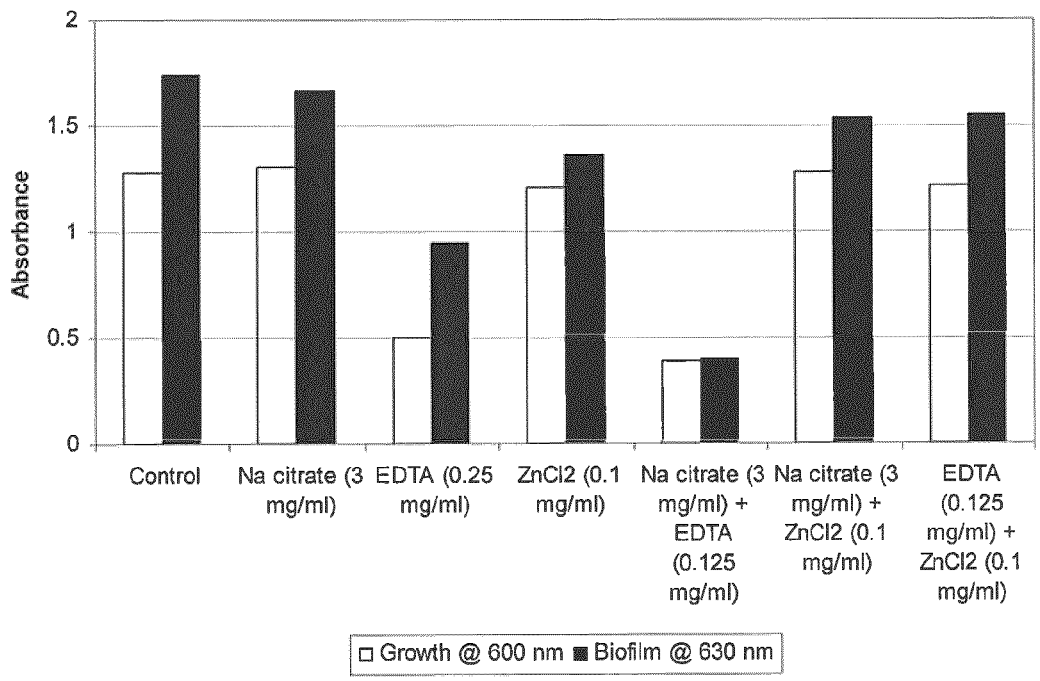
FIG. 19 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Proteus mirabilis* growth and biofilm formation

An overnight broth culture of *P. mirabilis* was grown in TSB and used as inoculum. 96-well microtiter plates containing TSB in the absence and the presence of each compound (sodium citrate or EDTA or Zinc chloride) separately and sodium citrate+EDTA, sodium citrate+ZnCl$_2$, and EDTA+ZnCl$_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 19).

Example 20

Inhibitory Effect of Sodium Citrate, EDTA and ZnCl$_2$ Alone, and Sodium Citrate+EDTA, Sodium Citrate+ZnCl$_2$, and EDTA+ZnCl$_2$ Combinations on *Candida albicans*

Figure 20:
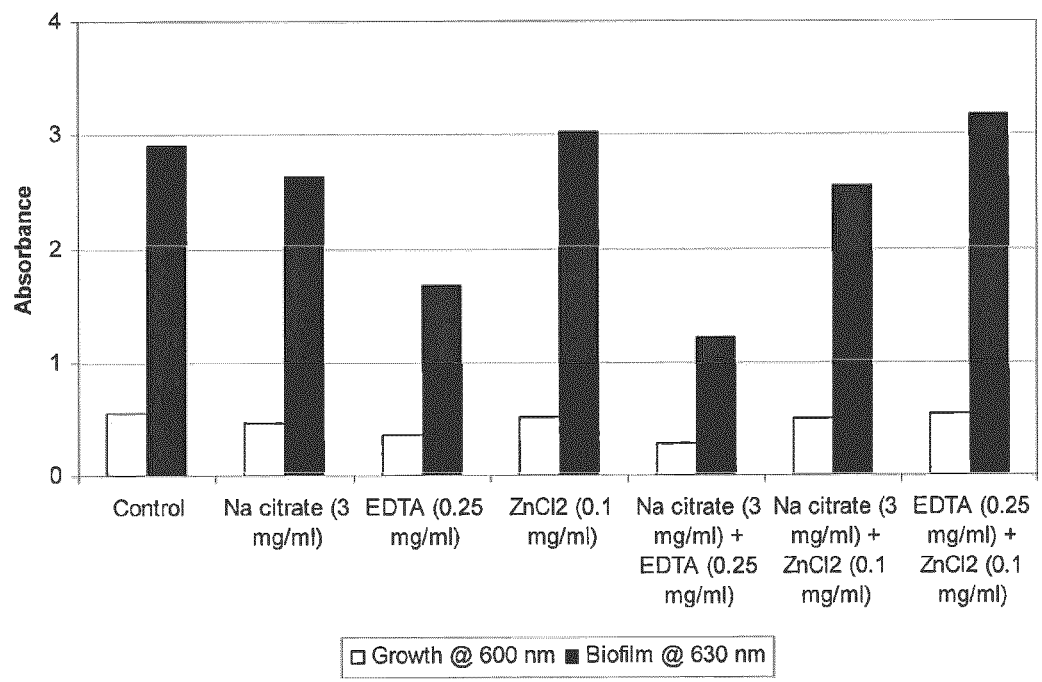
FIG. 20 is a bar graph showing the inhibitory effect of sodium citrate (3 mg/ml), EDTA (0.25 mg/ml) and $ZnCl_2$ (0.1 mg/ml) alone, and sodium citrate+EDTA, sodium citrate+$ZnCl_2$, and EDTA+$ZnCl_2$ combinations on *Candida albicans* growth and biofilm formation

An overnight broth culture of *C. albicans* was grown in TSB and used as inoculum. 96-well microtiter plates containing TSB in the absence and the presence of each compound (sodium citrate or EDTA or Zinc chloride) separately and sodium citrate+EDTA, sodium citrate+ZnCl$_2$, and EDTA+ZnCl$_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA combination showed an enhanced inhibitory effect on biofilm formation, as compared to sodium citrate, or EDTA alone (FIG. 20).

Example 21

Inhibitory Effect of Sodium Citrate, EDTA and ZnCl$_2$ Alone, and Sodium Citrate+EDTA, Sodium Citrate+ZnCl$_2$, and EDTA+ZnCl$_2$ Combinations on *Malassezia pachydermatis*

Figure 21:
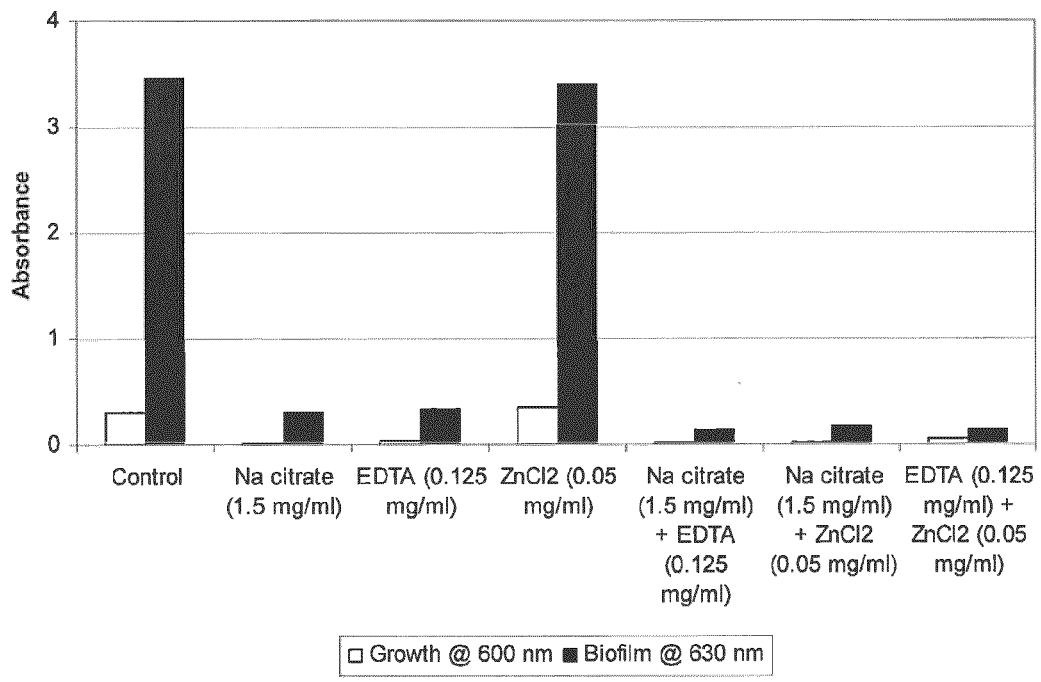
FIG. 21 is a bar graph showing the inhibitory effect of sodium citrate (1.5 mg/ml), EDTA (0.125 mg/ml) and $ZnCl_2$ (0.05 mg/ml) alone, and sodium citrate+EDTA, sodium citrate+$ZnCl_2$, and EDTA+$ZnCl_2$ combinations on *Malassezia pachydermatis* growth and biofilm formation

An overnight broth culture of *Malassezia pachydermatis* was grown in Sabouraud Dextrose Broth and used as inoculum. 96-well microtiter plates containing TSB in the absence and the presence of each compound (sodium citrate or EDTA or Zinc chloride) separately and sodium citrate+EDTA, sodium citrate+ZnCl$_2$, and EDTA+ZnCl$_2$ combinations were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A Sodium citrate+EDTA, Sodium citrate+ZnCl2, and EDTA+ZnCl2 combinations showed an enhanced inhibitory effect on biofilm formation, as compared to sodium citrate, or EDTA or zinc chloride alone (FIG. 21).

Example 22

Inhibitory Effect of Sodium Citrate, EDTA and ZnCl$_2$ Alone and in Combination on *Malassezia pachydermatis*

Figure 22:
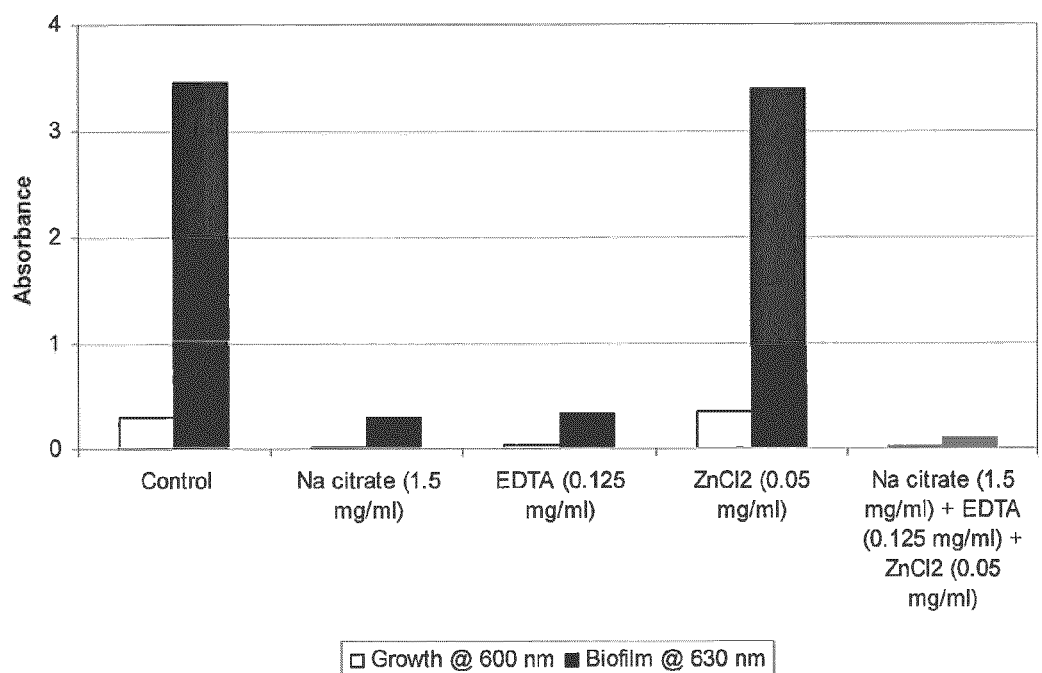
FIG. 22 is a bar graph showing the inhibitory effect of sodium citrate (1.5 mg/ml), EDTA (0.125 mg/ml) and $ZnCl_2$ (0.05 mg/ml) alone and in combination on *Malassezia pachydermatis* growth and biofilm formation

An overnight broth culture of *Malassezia pachydermatis* was grown in Sabouraud Dextrose Broth and used as inoculum. 96-well microtiter plates containing TSB in the absence and the presence of each compound (sodium citrate or EDTA or Zinc chloride) separately and together (Sodium chloride+EDTA+Zinc chloride) were inoculated and incubated at 37° C. for 24 hours. Growth of planktonic cells based on absorbance at 600 nm using Labsystems Multiskan Ascent microplate reader was determined. Biofilm was measured by discarding the media in the wells, rinsing the well three times with water, and staining the bound cells with crystal violet. The dye was then solubilized with 33% acetic acid, and absorbance at 630 nm was determined using a microtiter plate reader. A composition comprising sodium citrate, EDTA, and $ZnCl_2$ showed an enhanced inhibitory effect on biofilm formation, as compared to sodium citrate, or EDTA, or zinc chloride alone (FIG. 22).

We claim:

1. A composition for inhibiting growth of *Methicillin*-resistant *Staphylococcus aureus, Staphylococcus epidermidis, Streptococcus agalactiae* ATCC 12386, *Acinetobacter baumannii, Stenotrophomonas maltophilia,* Vancomycin-resistant Enterococci, or *Proteus mirabilis,* or for inhibiting biofilm formation by *Methicillin*-resistant *Staphylococcus aureus, Methicillin*-resistant *Staphylococcus* pseudintermedius, *Pseudomonas aeruginosa, Salmonella choleraesuis* ATCC 10708, *Escherichia coli* 0157:H7, *Staphylococcus epidermidis,* Coagulase-negative *Staphylococci, Streptococcus agalactiae* ATCC 12386, *Klebsiella pneumoniae, Acinetobacter baumannii, Stenotrophomonas maltophilia, Vancomycin*-resistant Enterococci, *Enterococcus faecalis, Proteus mirabilis,* or *Malassezia pachydermatis,* the composition comprising:
    (a) water;
    (b) one or more chelating agents selected from the group consisting of disodium or tetrasodium EDTA at a concentration of about 125 to 250 mg/L,
    (c) one or more chelating agents selected from the group consisting of sodium citrate, and potassium citrate, at a concentration of about 3,000 mg/L; and optionally
    (d) a zinc salt selected from the group consisting of zinc chloride, zinc gluconate, zinc lactate, zinc citrate, zinc sulfate, and zinc acetate.

2. The composition of claim 1, wherein the zinc salt is zinc chloride or zinc citrate.

3. The composition of claim 1, wherein the composition comprises:
    (i) disodium EDTA and sodium citrate, or
    (ii) sodium citrate, disodium EDTA and zinc chloride.

4. The composition of claim 1, further comprising an antimicrobial preservative selected from one or more of potassium sorbate, potassium benzoate, sodium benzoate and benzoic acid.

5. The composition of claim 1, further comprising one or more ingredients selected from the group consisting of: water, a buffer, a stabilizing agent, a gelling agent, a surfactant, a herbal, a vitamin, a mineral, an extra cellular matrix, an antimicrobial, an antibiotic, and a pH adjuster.

6. The composition of claim 1 prepared as one or more of a disinfecting solution, a dip solution, a lotion, a cream, an ointment, a gel, and a spray.

7. The composition as claimed in claim 1, wherein the composition comprises a liposome or nanoparticle or a suitable device delivery system.

8. The composition as claimed in claim 1, further comprising an anti-infective compound selected from the group consisting of glycoside hydrolase of Aggregatibacter *actinomycetemcomitans,* alginate lyase, nisin, lactoferricin, serotransferrin, ovotransferrin, ovalbumin, ovomucoid, protamine sulfate, chlorhexidine, cetylpyridinium chloride, triclosan, silver sulfadiazine, benzalkonium chloride, hydrogen peroxide, citric acid, potassium citrate, 5-fluorouracil, cis-2-decenoic acid, DNase I, proteinase K, silver, gallium, silver, bacteriocins and antimicrobial peptides.

9. The composition as claimed in claim 1 further comprising one or more of viscosity enhancing agents, lubricants, surfactants, buffers, preservatives, and salts.

10. The composition as claimed in claim 1, wherein the composition is selected from a solution, a gel, a cream, a jelly, a powder, a paste, a lotion, a soap and a cleaner.

11. A method of preventing or treating ophthalmic biofilm growth, the method comprising administering the composition of claim 1 to the eye of a user.

12. A method of preventing or treating hand or feet biofilm growth, the method comprising administering the composition of 1 to a foot, fingernail, or toenail of a user.

13. A personal care device treated or impregnated with the composition of claim 1.

14. The personal care device of claim 13, comprising one or more of a contact lens and a contact lens container.

15. The personal care device of claim 13, comprising one or more of a hand washing container, a scrubber, and a foot washing container.

* * * * *